(12) United States Patent
Jaroszeski et al.

(10) Patent No.: US 12,722,001 B1
(45) Date of Patent: Sep. 1, 2026

(54) DEVICE AND METHOD FOR THE DELIVERY OF MOLECULES INTO CELLS

(71) Applicant: University of South Florida, Tampa, FL (US)

(72) Inventors: Mark Jeffrey Jaroszeski, Wesley Chapel, FL (US); Richard Heller, Tampa, FL (US)

(73) Assignee: University of South Florida, Tampa, FL (US)

( * ) Notice: Subject to any disclaimer, the term of this patent is extended or adjusted under 35 U.S.C. 154(b) by 1220 days.

(21) Appl. No.: 17/341,915

(22) Filed: Jun. 8, 2021

Related U.S. Application Data

(63) Continuation-in-part of application No. 17/335,638, filed on Jun. 1, 2021.

(60) Provisional application No. 63/035,903, filed on Jun. 8, 2020, provisional application No. 63/032,889, filed on Jun. 1, 2020.

(51) Int. Cl.

| | |
|---|---|
| ***A61N 1/32*** | (2006.01) |
| ***A61N 1/40*** | (2006.01) |
| ***A61N 1/44*** | (2006.01) |
| ***C12N 13/00*** | (2006.01) |
| ***C12N 15/87*** | (2006.01) |

(52) U.S. Cl.
CPC ............... *A61N 1/327* (2013.01); *A61N 1/40* (2013.01); *A61N 1/44* (2013.01); *C12N 13/00* (2013.01); *C12N 15/87* (2013.01)

(58) Field of Classification Search
CPC . A61N 1/327; A61N 1/40; A61N 1/44; C12N 13/00; C12N 15/87
See application file for complete search history.

(56) References Cited

U.S. PATENT DOCUMENTS

| | | | | |
|---|---|---|---|---|
| 6,929,949 | B1 | 8/2005 | Hoff et al. | |
| 8,348,942 | B1 | 1/2013 | Jaroszeski et al. | |
| 8,455,228 | B2 | 6/2013 | Jaroszeski et al. | |
| 10,070,914 | B2 | 9/2018 | Schoenbach et al. | |
| 10,363,093 | B2 * | 7/2019 | Schoenbach | A61B 18/18 |
| 10,660,693 | B2 * | 5/2020 | Schoenbach | A61N 1/403 |
| 10,695,127 | B2 * | 6/2020 | Nuccitelli | A61N 1/326 |
| 10,765,850 | B2 * | 9/2020 | Kalghatgi | A61K 9/0021 |
| 2008/0097279 | A1 | 4/2008 | Sugawara | |
| 2013/0184693 | A1 | 7/2013 | Neev | |
| 2014/0364797 | A1 * | 12/2014 | Schoenbach | A61B 18/1206 606/41 |

OTHER PUBLICATIONS

ECA Academy, What are the regulatory Definitions for “Ambient”, “Room Temperature” and “Cold Chain”?, Feb. 3, 2017 (Year: 2017 ).*

(Continued)

*Primary Examiner* — William H. Beisner
*Assistant Examiner* — Danielle B Henkel
(74) *Attorney, Agent, or Firm* — Molly L. Sauter; Trenam Law

(57) ABSTRACT

A system and method for molecular delivery in vitro, ex vivo, or in vivo applications using a synergistic effect of corona charge treatment and elevated temperatures. Applications of the invention include cell death and biological particle destruction/inactivation, including, but not limited to viruses and prions.

6 Claims, 3 Drawing Sheets

(56) References Cited

OTHER PUBLICATIONS

Connolly, R. J. et al., Plasma Facilitated Delivery of DNA to Skin, Biotechnology and Bioengineering, vol. 104, No. 5, Dec. 1, 2009, pp. 1034-1040.
Connolly, R. J. et al., Enhancement of antigen specific humoral immune responses after delivery of a DNA plasmid based vaccine through a contact-independent helium plasma, Vaccine, 29 (2011) 6781-6784.
Connolly, R. J. et al., Characterization of plasma mediated molecular delivery to cells in vitro, International Journal of Pharmaceutics, 389 (2010) 53-57.
Connolly, R. J. et al., Non-contact helium-based plasma for delivery of DNA vaccines, Human Vaccines & Immunotherapeutics, 8:11 (2012) 1729-1733.
Connolly, R. J. et al., Optimization of a plasma facilitated DNA delivery method, Bioelectrochemistry, 103 (2015) 15-21.
Donate, A. et al., Thermal Assisted In Vivo Gene Electrotransfer, Curr Gene Ther., (2016) 16(2): 83-89.
Donate, A. et al., Application of increased temperature from an exogenous source to enhance gene electrotransfer, Bioelectrochemistry, 103 (2015) 120-123.
Edelblute, C. M. et al., Plasma-activated air mediates plasmid DNA delivery in vivo, Molecular Therapy—Methods & Clinical Development (2016) 3, 16028.
Edelblute, C. M. et al., Activated Air Produced by Shielded Sliding Discharge Plasma Mediates Plasmid DNA Delivery to Mammalian Cells, Biotechnology and Bioengineering, (2015) 112: 2583-2590.
Jaroszeski, M. J. et al., Direct Current Helium Plasma for In vivo Delivery of Plasmid DNA Encoding Erythropoietin to Murine Skin, Plasma Medicine, (2017) 7(3):261-271.
Ramachandran, N. et al., Molecular Delivery to Cells Facilitated by Corona lon Deposition, IEEE Transactions on Nanobioscience, (2008) 7(3): 233-239.
Shah, K. et al., Electrogenetherapy of B16.F10 murine melanoma tumors with an interleukin-28 expressing DNA plasmid, Human Vaccines & Immunotherapeutics, (2012) 8:11, 1722-1728.

* cited by examiner

DEVICE AND METHOD FOR THE DELIVERY OF MOLECULES INTO CELLS

CROSS-REFERENCE TO RELATED APPLICATIONS

This application is a continuation-in-part of, and claims priority to, U.S. Non-Provisional patent application Ser. No. 17/335,638, entitled "Method and Device for Hair Removal, Hair Growth Reduction or Hair Growth Elimination," filed Jun. 1, 2021, which claims priority to U.S. Provisional Patent Application No. 63/032,889, entitled "System and Method Using Charge Stream at Elevated Temperatures for the Treatment of Skin and Other Tissues to Remove Hair, Reduce Hair Growth, or Eliminate Hair Growth," filed Jun. 1, 2020. This application also claims priority to U.S. Provisional Patent Application No. 63/035,903, entitled "System and Method Using Charge Stream Combined with Elevated Temperatures to Deliver Molecules to Cells," filed Jun. 8, 2020.

BACKGROUND OF THE INVENTION

Various methods are known in the art for using electrical charge to effectively delivery molecules into the interior of cells, including, but not limited to electroporation techniques. Charged streams have been used as forcing functions to affect cells in such a way that they can uptake exogenous molecules. However, replication of the results in the current state of the art has been difficult.

Accordingly, what is needed in the art is an improved method for the delivery of molecules to cells in vitro and in vivo.

SUMMARY OF THE INVENTION

In various embodiments, the present invention provides a system and method for molecular delivery into cells using a synergistic effect of corona charge treatment and elevated temperatures. Applications of the invention include cell death and biological particle destruction/inactivation, including, but not limited to viruses and prions.

In one embodiment, the present invention provides a method for the delivery of molecules into the interior of cells which includes, heating a tissue of interest comprising a plurality of cells and directing a stream of charged gas particles at the tissue of interest to deliver one or more molecules into the interior of one or more of the plurality of cells. The heating of the tissue of interest and directing the stream of charged gas particles at the tissue of interest may be performed in vitro, ex vivo, and in vivo and the one or more molecules may include, but are not limited to, deoxyribonucleic (DNA), ribonucleic acid (RNA), nucleic acids, chemo agents and other drugs.

The heating of the tissue and the application of the stream of charged gas particles may be accomplished sequentially or substantially simultaneously.

The thermal charged stream maybe a thermal plasma charged stream or a thermal coronal charged stream, wherein the stream itself is effective in heating the tissue of interest.

The heating of tissue of interest may be accomplished using infrared, laser, microwave, radio waves, warm air or through contact with a heated surface.

In a particular embodiment, directing the stream of charged gas particles at the tissue of interest may include, positioning an electric field generating device proximate to the tissue of interest, wherein the electric field generating device comprises at least one electrode, positioning a gas source in fluid communication with the electric field generating device, applying a first electric potential to the at least one electrode and establishing a second potential by flowing the gas source past the electrode during the application of the first potential.

In an additional embodiment, the present invention provides a device for delivery of molecules into the interior of cells which includes, a heat source configured to heat a tissue of interest comprising a plurality of cells and an applicator for directing a stream of charged gas particles at the tissue of interest. The applicator may further include, a hollow body having a first and a second end, a gas source in fluid communication with the first end of the hollow body, wherein the gas source supplies a flow of gas through the hollow body and an electrode secured to the second end of the hollow body, wherein the electrode is connected to a power supply to generate an electric field and to ionize gas from the gas source and wherein the electric field is created using a constant direct current (DC) voltage.

The device may be used to deliver deoxyribonucleic (DNA), ribonucleic acid (RNA), nucleic acids, chemo agents and other drugs to the interior of the tissue cells.

The heat source may include infrared, laser, microwave, radio waves, warm air or contact with a heated surface, wherein the heat from the heat source does not substantially affect the viability of the plurality of cells.

The heat source and the applicator for directing the charged stream may be used sequentially or substantially simultaneously.

As such, in accordance with the various embodiments of the present invention, an improved system and method are provided for delivering molecules into the interior of cells.

DETAILED DESCRIPTION OF THE INVENTION

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention. For example, charge from many sources can be applied to achieve the same effects. These can include but are not limited to: corona charge, DC plasma, AC plasma, RF plasma, plasma formed from any gas (including air), plasma formed from any mixture of two or more gasses, and electrospray technology.

In various embodiments, the present invention provides a system and method for using the synergistic effect of corona charge treatment and elevated temperatures for molecular delivery in vitro, ex vivo, and in vivo applications. It is shown that the use of corona charge treatment combined with elevated temperatures results in an increase in molecular delivery to a T-cell line compared to no treatment, coronal charge alone, and elevated temperature alone.

Figure 1:
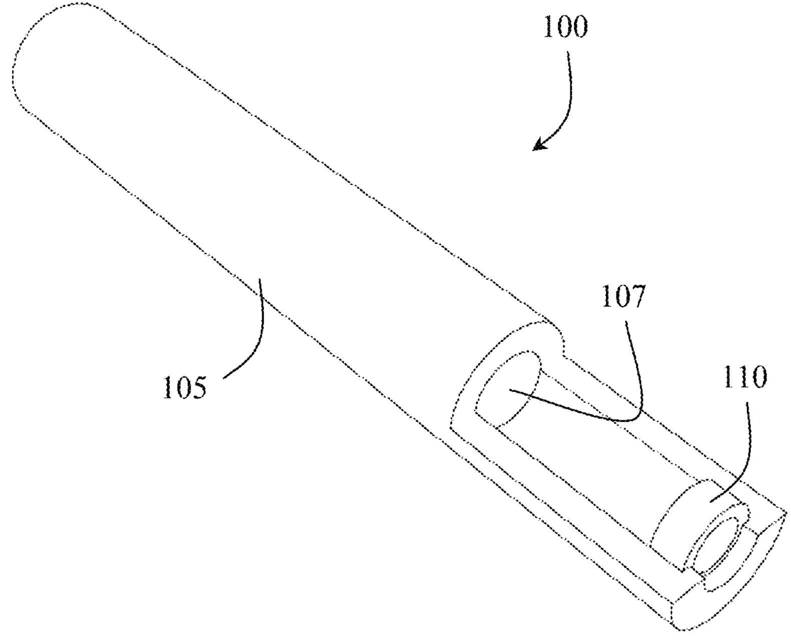
FIG. 1 is a perspective view of a device for directing a stream of charged gas particles at a tissue of interest, in accordance with an embodiment of the present invention.

Referring now to FIG. 1, a device 100 for directing a stream of charged gas particles to the tissue of interest may include a tube 105 having an inner channel 107. The tube 105 may be approximately 15 cm long and the diameter of the inner channel 107 may be approximately 1 cm. Annular electrode 110 is positioned substantially at the opening of the tube 105. The tube 105 is connected to a high-voltage and low-current direct current power supply. In this embodiment, an electric potential is applied to electrode 110, depending upon the desired polarity and a stream of ultra-high purity helium (He) is passed through the inner channel 107 and past the electrode 110. A stream of charged gas particles, such as a corona charge is specifically a plasma made using ambient air, whereas a plasma is typically the name used when other gasses (such as helium) are used to generate a charged stream.

Figure 2:
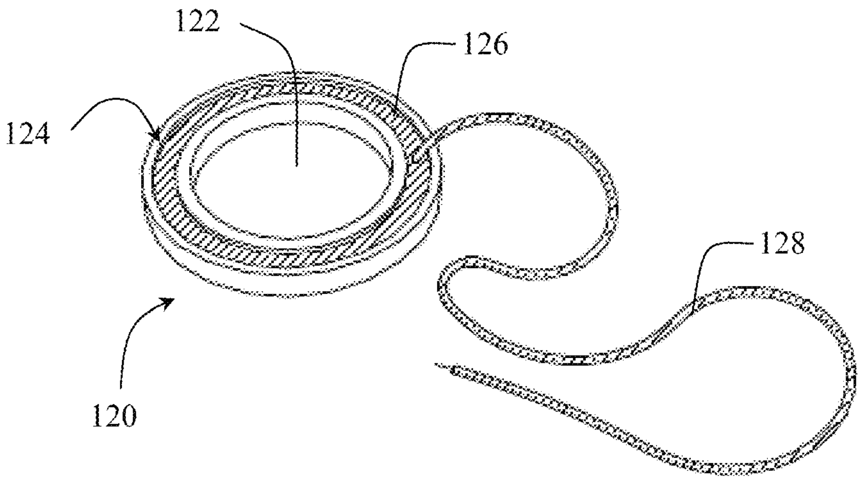
FIG. 2 is a perspective view of a conductive ring to surround a portion of the tissue of interest, in accordance with an embodiment of the present invention.

As shown in FIG. 2, in an experimental embodiment, a culture dish 120 used in conjunction with the device for directing a stream of charged gas particles to the tissue of interest 100 may include an inner chamber 122 and an outer chamber 124. The inner chamber 122 is adapted to hold a biological structure, such as a tissue of interest, and the outer chamber 124 is adapted to receive a conductive ring 126 which is connected to a ground potential through a wire 128. The conductive ring 126 and the wire 128 can be made from any conductive material as is known in the art. In operation, the grounding ring 126 can be placed directly on the tissue of interest and may be used to concentrate the stream of charged gas particles onto a desired portion of the tissue of interest.

Figure 3:
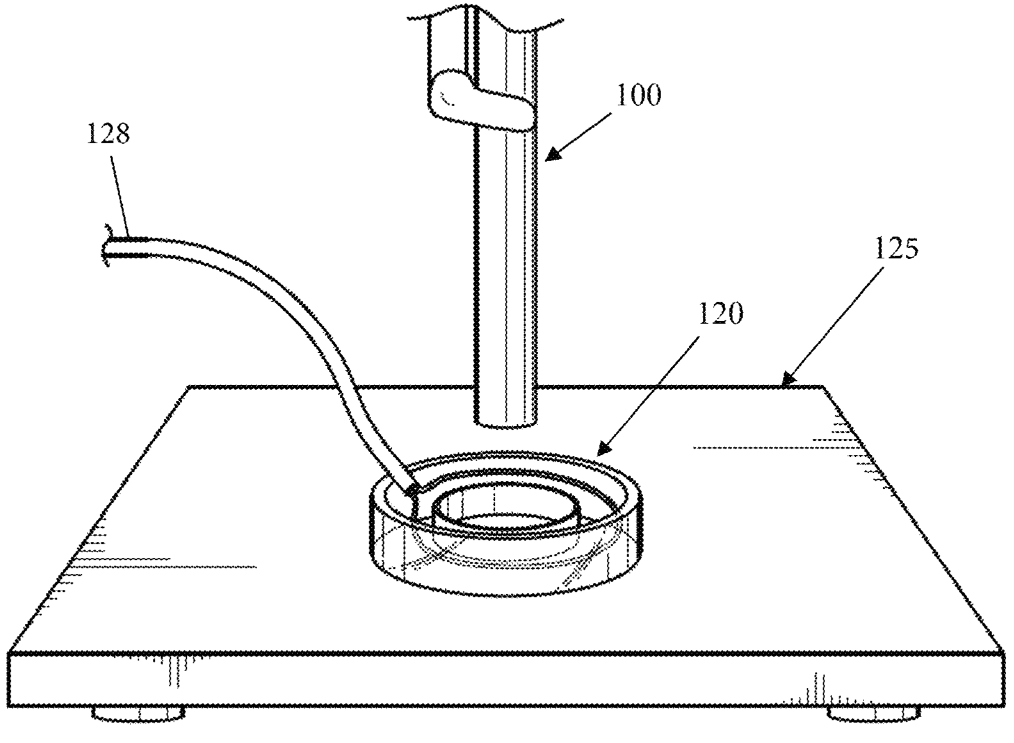
FIG. 3 is perspective view of the device for directing a stream of charged gas particles at a tissue of interest and a conductive ring to surround a portion of the tissue of interest, in accordance with an embodiment of the present invention.

As additionally shown in FIG. 3, in an experimental exemplary embodiment a hot plate 125 may be positioned below, and in contact with, the culture dish 120 to provide heating of the tissue of interest prior to, or during, the application of the stream of charged gas particles to the target of interest by the device 100.

Figure 4:
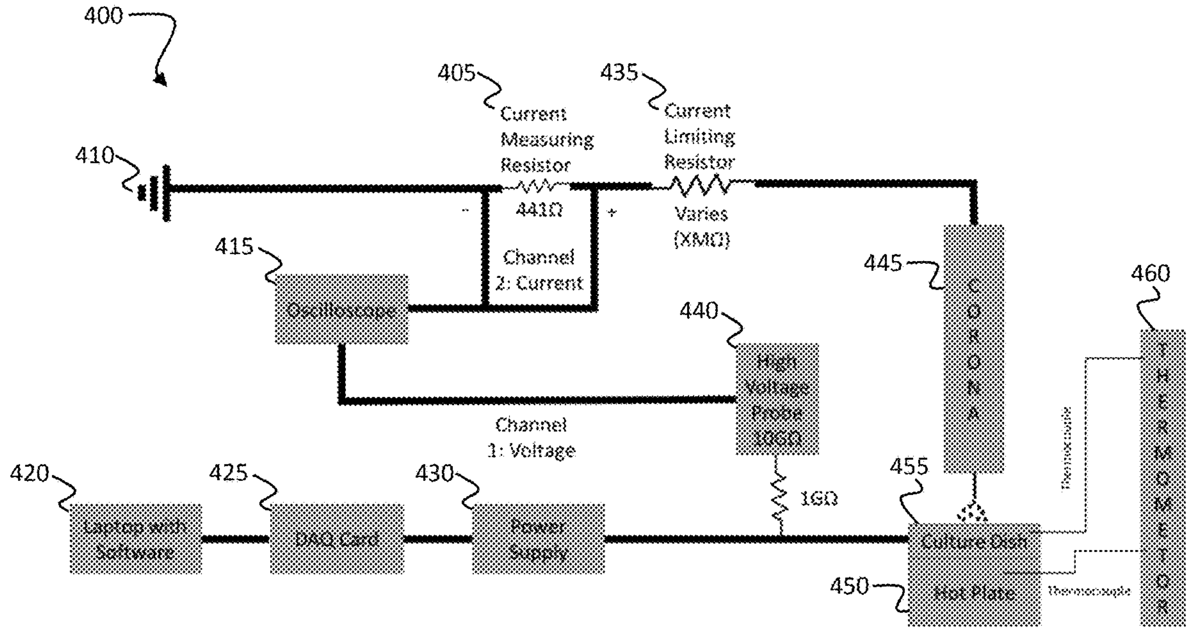
FIG. 4 illustrates an apparatus and electrical circuitry for heating cell of a tissue of interest in a cell culture dish and treating the cells with a stream of charged gas particles (i.e., corona charge) in accordance with an embodiment of the present invention.
Figure 5:
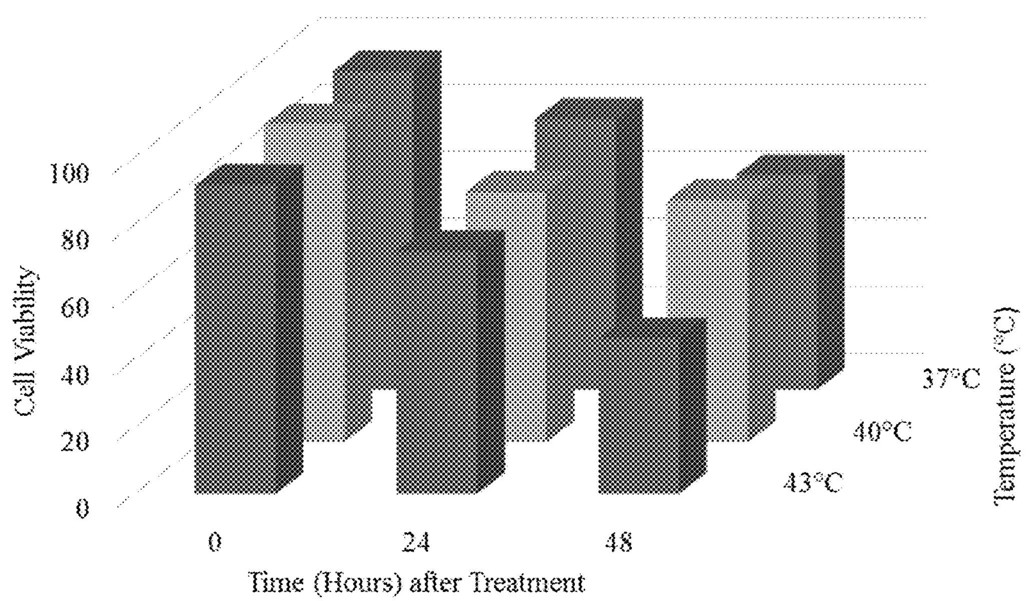
FIG. 5 is a graphical illustration of the viability of cells of a tissue of interest that were first heated to 37°, 40°, and 43° C. and then treated for 3 minutes with corona charge (10 kV and 25 μA). Viability was determined at hours 0, 24, and 48 with N=3 samples per temperature.

As shown in FIG. 4, an exemplary system 400 for molecular delivery is illustrated. The system 400 includes a current measuring resistor 405 in series with a current limiting resistor 435, which are coupled between a ground potential 410 and a corona device 445 for directing a stream of charged gas particles to the culture dish 455. A high voltage probe 440 allows the oscilloscope 415 to monitor the output of the power supply 430. A data acquisition module 425 and computer processor running software 420 are used to control the output of the power supply 430. A hot plate 450 is positioned below, and in contact with, the culture dish 455 for heating the tissue of interest contained within. A thermometer 460 is used to monitor and control the heat provided by the hot plate 450.

In operation, the culture dish 455 is heated by the hot plate 450 to a desired temperature and the corona device 455 directs a stream of charged gas particles to a tissue in the culture dish 455. The combined heating and charged stream are effective in delivering one or more molecules into the interior of the cells of the tissue. As such, it is envisioned that applying plasma/corona charge, hereafter referred to as a charged stream, to skin combined with heating the skin moderately (from 30° C. to 55° C.) results in delivery of molecules into the cells of the skin.

In an exemplary embodiment, human Jurkat cells (Clone E6-1 cells, ATCC TIB-152, American Type Culture Collection Manassas, VA) are immortalized human T lymphocytes and were used in experiments described below. They were cultured in RPMI 1640 1× with L-glutamine (11875093, Gibco, Grand Island, New York). Media was supplemented with 10% (v/v) Fetal Bovine Serum (Corning 35011CV, Corning Cellgro, New York, New York), 1% (v/v) 200 mM L-glutamine (25030081, Gibco), and 1% (v/v) penicillin-streptomycin (15140122, Gibco). The cells were seeded in 75 $cm^2$ flasks (Corning 430641, Corning Cellgro) and grown in a standard 37° C. incubator that had a humified environment that contained 5% $CO_2$.

Sytox™ Green Nucleic Acid Stain (S7020, Life Technologies, Eugene, Oregon) was used as a tracer molecule because it fluoresces when it comes into contact with nucleic acids. This can only occur if the membrane of the cell is compromised (i.e., the cell is dead or the corona charge permeabilizes a cell membrane to allow the molecule into the cell). Once the molecule comes into contact with the nucleic acid, the fluorescence increases by more than 500-fold and was detected in cellular samples using a BioTek FLx800 Microplate Fluorescence Reader (BT-FLX800T, BioTek, Winooski, VT). Cell cultures were exposed to 1 μM Sytox™ as part of the molecular delivery procedures.

Modified organ culture double-well dishes (Falcon 353037, Corning) were used for experimentation. FIG. 3 illustrates an example dish which was sputter-coated with gold so that the resulting layer was approximately 100 Angstroms thick. Dishes were first sputter-coated with chrome. The chrome helped keep the gold attached to the dish. Then, with the exception of the center well where the cell suspension would ultimately be treated, the dish was coated in Matte Clear Enamel (7701830, Rust-Oleum, Vernon Hills, IL). This was to ensure that the corona charge would not arc or stream to parts of the dish other than the flat cell culture surface that was at the bottom of the center well. Once the enamel was dry, a layer of electrical tape was placed on the inside of the outer well to ensure even if the enamel wore off that there would still be a barrier. Kapton tape was placed around the outside of the outer well for the same purpose. Once the dish was well insulated, a piece of copper tape was placed so that it contacted the uninsulated cell treatment area and formed a pathway to the exterior of the dish. This piece of tape was connected to the high voltage power supply.

Corona charge was generated by arranging a single 28-gauge acupuncture needle in a holder over the center of the cell culture surface and connecting the needle to ground through resistance. The needle and holder are shown in FIG. 1.

During heating and corona charge exposure, each dish containing cells was placed into an electrical circuit and apparatus depicted in FIG. 4. The dish 455 was heated by a hotplate 450 until an appropriate temperature was attained. Corona charge was then applied for 3 minutes at a voltage of 10 kV with 25 μA current flowing in the corona charge generating electrical circuit 445. Temperatures of 37° C., 40° C., and 43° C. were used.

Experimental data showed that heating 40° C. and 43° C. for between 2 and 5 minutes did not affect cell viability as compared to cell viability at 37° C. Elevated temperatures (40° C. and 43° C.) for between 2 and 5 minutes did not cause statistically significant delivery. When cells were treated with corona charge for 3 minutes after first being heated to 40° C. and 43° C. their viability was not significantly affected when compared to cells treated with corona charge at 37° C. as shown in FIG. 4. However, Table 1 shows that when corona charge was used to deliver Sytox™ at these same two elevated temperatures.

Table 1 shows fluorescence data (delivery) that occurred when corona charge was used to deliver Sytox™ at the same two elevated temperatures (40° C. and 43° C.). Analysis indicates that larger differences in mean fluorescence (delivered Sytox™) were seen as temperatures increased from room temperature to 40° C. However, the mean fluorescence of all samples exposed to room temperature, 37° C., and 40° C. was very similar. This indicates a synergistic effect of temperature on delivery using corona charge, which is unexpected.

TABLE 1

Mean Fluorescence and Standard Deviations for Control (heated only) and Treated (Heated + Corona charge) at Varying Temperatures

| | | Control (Heated Only) | | Treated (Heat and Corona) | | Difference | |
|---|---|---|---|---|---|---|---|
| Temp (° C.) | N | Mean Fluorescence | Standard Deviation | Mean Fluorescence | Standard Deviation | Mean Fluorescence | Standard Deviation |
| RT | 3 | 750.67 | 39.40 | 837.22 | 7.24 | 86.56 | 32.22 |
| 37 | 9 | 717.04 | 48.12 | 844.04 | 76.45 | 127.00 | 87.03 |
| 40 | 14 | 745.83 | 90.80 | 938.98 | 87.31 | 193.14 | 122.71 |
| 43 | 8 | 1040.25 | 155.90 | 1165.29 | 166.25 | 125.04 | 77.91 |

As such, short-term heating of tissues/cells has been shown to increase molecular delivery resulting from traditional electrical treatment of cells with DC pulses in tissues and when corona charge has been applied to cells. It is likely that temperature increases may increase the effects of charged streams that are typically atmospheric plasmas (coronal charge) or plasmas. Moderate heating may have benefit to treating tissues with plasma/corona for the for the delivery of molecules into the tissue cells as it may increase the capacity of the charged stream to have detrimental effects on the cells. The art teaches away from heating living cells as it can cause negative effects on skin/tissue.

As such, while charged streams have been used as forcing functions to affect tissues in such a way as to delivery molecules into the cells, in the present invention, a mild temperature increase is added to the treatment to improve the results of the charged stream.

In an exemplary embodiment, the tissue may be heated prior to the application of the charged stream. In particular, the tissue may be heated to a temperature between about 30° C. to 55° C. prior to the application of the stream. In an alternative embodiment, the tissue may be heated during the application of the charged stream. In a particular embodiment, the heat may be applied to elevate the temperature above ambient but below a maximum of about 45° C.

Optionally, the tissue may be heated through the application of a thermal charged stream, such as thermal plasma and/or thermal coronal charge.

Corona charge can be made from ambient air. Additionally, plasma (a charge stream made from gasses other than air) can be made from a single gas or mixture of gasses including air. The corona charge and/or plasma may be generated by flowing gases or pumped gases.

The heat may be supplied from various sources, including, but not limited to, an infrared source, microwave or similar antenna, warm air, heat supplied by the corona charge or plasma stream itself, heat supplied by various types of electrical signals used to generate corona charge or plasma (AC, DC, combined AC and DC) in any waveform, such as rectangular, bipolar, etc.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A device for delivery of molecules into the interior of cells, the device comprising:

a heat source configured to heat a tissue of interest comprising a plurality of cells to an elevated temperature between 40° C. and 43° C. for a duration of between 2 minutes and 5 minutes;

an applicator for directing a stream of charged gas particles at the tissue of interest that has been heated to the elevated temperature to deliver one or more molecules into an interior of one or more of the plurality of cells, wherein the applicator is not in contact with the tissue of interest, the applicator comprising;

a hollow body having a first and a second end;

a gas source in fluid communication with the first end of the hollow body, wherein the gas source supplies a flow of gas through the hollow body; and an electrode secured to the second end of the hollow body, wherein the electrode is connected to a power supply to generate an electric field and to ionize gas from the gas source, wherein the electric field is created using a constant direct current (DC) voltage.

2. The device of claim 1, wherein the one or more molecules are selected from deoxyribonucleic (DNA), ribonucleic acid (RNA), nucleic acids, chemo agents and other drugs.

3. The device of claim 1, wherein the heat source for heating the tissue of interest does not substantially affect the viability of the plurality of cells.

4. The device of claim 1, wherein the heat source and the applicator for directing the stream of charged gas particles at the tissue of interest are applied sequentially.

5. The device of claim 1, wherein the heat source and the applicator for directing the stream of charged gas particles at the tissue of interest are applied substantially simultaneously.

6. The device of claim 1, wherein the heat source comprises one or more of infrared, laser, microwave, radio waves, warm air and contact with a heated surface.

* * * * *